US012611377B2

(12) United States Patent
Patel et al.

(10) Patent No.: US 12,611,377 B2
(45) Date of Patent: Apr. 28, 2026

(54) PHARMACEUTICAL COMPOSITION COMPRISING AN ANDROGEN RECEPTOR INHIBITOR

(71) Applicant: ONCOSOL LIMITED, Harrow (GB)

(72) Inventors: Nileshkumar Bhikhabhai Patel, Ahmedabad (IN); Lalchand Dataram Gurjar, Jaipur (IN); Jayanta Kumar Mandal, Ahmedabad (IN)

(73) Assignee: ONCOSOL LIMITED, Harrow (GB)

( * ) Notice: Subject to any disclaimer, the term of this patent is extended or adjusted under 35 U.S.C. 154(b) by 0 days.

(21) Appl. No.: 18/397,458

(22) Filed: Dec. 27, 2023

(65) Prior Publication Data

US 2024/0122846 A1 Apr. 18, 2024

Related U.S. Application Data

(63) Continuation of application No. 16/326,850, filed as application No. PCT/IB2017/054945 on Aug. 14, 2017, now abandoned.

(30) Foreign Application Priority Data

Aug. 20, 2016 (IN) ............................ 201621028407

(51) Int. Cl.

| | |
|---|---|
| ***A61K 9/00*** | (2006.01) |
| ***A61K 9/08*** | (2006.01) |
| ***A61K 31/4166*** | (2006.01) |
| ***A61K 47/10*** | (2017.01) |
| ***A61K 47/14*** | (2017.01) |
| ***A61K 47/26*** | (2006.01) |

(52) U.S. Cl.

CPC .............. *A61K 9/0053* (2013.01); *A61K 9/08* (2013.01); *A61K 31/4166* (2013.01); *A61K 47/10* (2013.01); *A61K 47/14* (2013.01); *A61K 47/26* (2013.01)

(58) Field of Classification Search

CPC ...... A61K 47/10; A61K 31/4166; A61K 9/08; A61K 9/0053

See application file for complete search history.

(56) References Cited

U.S. PATENT DOCUMENTS

| | | | | |
|---|---|---|---|---|
| 7,709,517 | B2 * | 5/2010 | Sawyers | C07D 235/02 548/321.1 |
| 8,809,550 | B2 | 8/2014 | Tong | |
| 11,839,689 | B2 | 12/2023 | Lorenz et al. | |
| 2002/0003179 | A1 | 1/2002 | Verhoff et al. | |
| 2002/0119200 | A1 | 8/2002 | Haskell | |
| 2014/0066495 | A1 | 3/2014 | Ye et al. | |
| 2014/0371242 | A1 * | 12/2014 | Wang | A61K 31/52 514/263.2 |
| 2016/0346207 | A1 | 12/2016 | Grahek et al. | |

FOREIGN PATENT DOCUMENTS

| | | | | | |
|---|---|---|---|---|---|
| CN | 104857517 | | * | 8/2015 | |
| CN | 104857517 | B | | 4/2018 | |
| EP | 2659902 | A1 | | 11/2013 | |
| WO | WO 2007/126765 | | * | 8/2007 | |
| WO | 2007/126765 | A2 | | 11/2007 | |
| WO | 2012/029076 | A2 | | 3/2012 | |
| WO | WO-2015022349 | A1 | * | 2/2015 | A61K 9/48 |
| WO | 2015/042170 | A1 | | 3/2015 | |
| WO | 2015/114314 | A1 | | 8/2015 | |

OTHER PUBLICATIONS

Singh A K et al., "High performance liquid chromatography method for the pharmacokinetic study of bicalutamide SMEDDS and suspension formulations after oral administration to rats", Talanta vol. 78, No. 4-5: 1310-1314 (2009).

Hintzen Fabian et al., "In vivo evaluation of an oral self-microemulsifying drug delivery system (SMEDDS) for leuprorelin", International Journal of Pharmaceutics, vol. 472, No. 1 (2014).

Yin Y M et al., "Docetaxel microemulsion for enhanced oral bioavailability: Preparation and in vitro and in vivo evaluation", Journal of Controlled Release vol. 140, No. 2: 86-94 (2009).

XTANDI (enzalutamide) capsules, prescribing information (Oct. 2015), 21 pp.

International Search Report for International Application No. PCT/IB2017/054945 (Nov. 3, 2017).

* cited by examiner

*Primary Examiner* — Marcos L Sznaidman

(74) *Attorney, Agent, or Firm* — Merchant & Gould P.C.; Daniel R. Evans; Daniel J. Pereira

(57) ABSTRACT

The present invention relates to the oral pharmaceutical composition comprising an androgen receptor inhibitor and one or more pharmaceutically acceptable excipients selected from the group comprising of fillers/vehicles, solvents/co-solvents, preservatives/antioxidants, surfactants, buffering agents, chelating agents, sweetening agents, flavouring agents, sweetness/flavour enhancing agents, or combinations thereof. The present invention also relates to the processes for the preparation of the oral pharmaceutical composition comprising androgen receptor inhibitor and one or more pharmaceutically acceptable excipients.

20 Claims, No Drawings

PHARMACEUTICAL COMPOSITION COMPRISING AN ANDROGEN RECEPTOR INHIBITOR

This application is a continuation of U.S. patent application Ser. No. 16/326,850, which is a US National Stage Application of PCT/IB2017/054945, filed on Aug. 14, 2017, which claims priority to Indian Patent Application number 201621028407, filed on Aug. 20, 2016, the subject matter of which is incorporated by reference.

FIELD OF THE INVENTION

The present invention relates, in general, to the pharmaceutical field, and more precisely it relates to a pharmaceutical composition for the oral administration of Androgen Receptor Antagonists and to the process for the preparation thereof. In particular, the present invention relates to the oral liquid composition comprising Enzalutamide.

BACKGROUND OF THE INVENTION

The Androgen Receptor (AR), also known as NR3C4 (nuclear receptor subfamily 3, group C, member 4), is a type of nuclear receptor that is activated by binding either of the androgenic hormones, testosterone, or dihydrotestosterone in the cytoplasm and then translocating into the nucleus. The androgen receptor is most closely related to the progesterone receptor, and progestins in higher dosages can block the androgen receptor.

The main function of the androgen receptor is as a DNA-binding transcription factor that regulates gene expression; however, the androgen receptor has other functions as well. Androgen regulated genes are critical for the development and maintenance of the male sexual phenotype.

The Androgen Receptor is important for therapeutic target in prostate cancer, thus many different inhibitors have been developed, primarily targeting the ligand binding domain of the protein, while inhibitors that target the N-terminal domain of the protein are still under development. AR ligands can either be classified based on their structure (steroidal or non-steroidal) or based on their ability to activate or inhibit transcription (agonists or antagonists).

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, therefore, reducing the AR activity. Although initially effective, these treatments quickly fail and the cancer becomes hormone refractory.

Overexpression of AR has been identified and validated as a cause of hormone refractory prostate cancer. See Chen, C. D., Welsbie, D. S., Tran, C., Baek, S. H., Chen. R., Vessella, R., Rosenfeld. M. G., and Sawyers, C. L., Molecular determinants of resistance to an antiandrogen therapy, Nat. Med., 10: 33-39, 2004, which is hereby incorporated by reference. Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explains why castration and anti-androgens fail to prevent prostate cancer progression and reveals unrecognized properties of hormone refractory prostate cancer.

Antigonadotropins like estrogens and progestogens were both first introduced in the 1930s. AR antagonists were first discovered in the early 1960s. The steroidal antiandrogen-cyproterone acetate was discovered in 1961 and introduced in 1973 and is often described as the first antiandrogen to have been marketed. However, spironolactone was introduced in 1959, and although its antiandrogen effects were not recognized or taken advantage of until later and were originally an unintended off-target action of the drug, it may be more appropriate to regard it as the first antiandrogen to have been introduced. In addition to spironolactone, chlormadinone acetate and megestrol acetate are steroidal antiandrogens that are weaker than cyproterone acetate but were also introduced earlier, in the 1960s. Other early steroidal antiandrogens that were developed around this time but were never marketed include benorterone (SKF-7690; 17α-methyl-B-nortestosterone). BOMT (Ro 7-2340), cyproterone (SH-80881), and trimethyltrienolone (R-2956).

The nonsteroidalantiandrogenflutamide was first reported in 1967. It was introduced in 1983 and was the first nonsteroidalantiandrogen to be marketed. Another early nonsteroidalantiandrogen, DIMP (Ro 7-8117), which is structurally related to thalidomide and is a relatively weak antiandrogen, was first described in 1973 and was never marketed. Flutamide was followed by nilutamide in 1989 and bicalutamide in 1995. In addition to these three drugs, which have been regarded as first-generation nonsteroidal-antiandrogens, the second-generation nonsteroidalantiandrogen enzalutamide was introduced in 2012. It differs from the earlier nonsteroidalantiandrogens namely in that it is much more efficacious in comparison.

The androgen synthesis inhibitors aminoglutethimide and ketoconazole were first marketed in 1960 and 1977, respectively, and the newer drug abiraterone acetate was introduced in 2011. GnRH analogues were first introduced in the 1980s. The 5α-reductase inhibitors finasteride and dutasteride were introduced in 1992 and 2002, respectively.

A nonsteroidalantiandrogen (NSAA) is an antiandrogen with a nonsteroidal chemical structure. They are typically selective and full or silent antagonists of the androgen receptor (AR) and act by blocking the effects of androgens like testosterone and dihydrotestosterone (DHT). SAAs are used in the treatment of androgen-dependent conditions in men and women. They are the converse of steroidal antiandrogens (SAAs), which are antiandrogens that are steroids and are structurally related to testosterone.

Bicalutamide (brand name: Casodex®) is the most commonly used anti-androgen. While it has an inhibitory effect on AR in hormone sensitive prostate cancer, it fails to suppress AR when cancer becomes hormone refractory. Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Therefore, better AR inhibitors with more potent antagonistic activities and minimal agonistic activities are needed to delay disease progression and to treat the fatal hormone refractory prostate cancer.

Nonsteroidal anti-androgens, such as bicalutamide, have been preferred over steroidal compounds for prostate cancer because they are more selective and have fewer side effects. This class of compounds has been described in many patents such as U.S. Pat. No. 4,097,578. U.S. Pat. Nos. 5,411,981, 5,705,654, PCT International Applications WO 1997/00071 and WO 2000/17163, and U.S. Published Patent Application No. 2004/0009969, all of which are hereby incorporated by reference.

Other marketed non-steroidal anti-androgens include Flutamide (Eulexin®), Nilutamide (Anandron® and Nilandron®), Topilutamide (Eucapil®), Enzalutamide (Xtandi®); Cimetidine (Tagamet®). Under development non-steroidal anti-androgens include Apalutamide (ARN-509. JNJ-56021927), Darolutamide (ODM-201. BAY-1841788), Proxalutamide (GT-0918). These non-steroidal anti-androgens have been discontinued from the development: Cioteronel (CPC-10997), Inocoterone acetate (RU-38882, RU-882). RU-58841 (PSK-3841, HMR-3841).

Enzalutamide is an androgen receptor signaling inhibitor. The chemical name is 4-{3-[4-cyano-3-(trifluoromethyl) phenyl]-5,5-dimethyl-4-oxo-2-sulfanylideneimidazolidin-1-yl}-2-fluoro-N-methylbenzamide. The structural formula is:

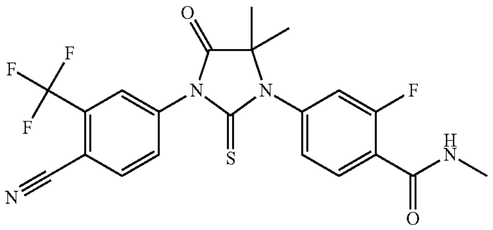 [SMILES: CNC(=O)c1ccc(N2C(=S)N(c3ccc(C#N)c(C(F)(F)F)c3)C(=O)C2(C)C)cc1F]

Enzalutamide is used as an agent for treating castration-resistant prostate cancer. See, e.g., U.S. Pat. No. 7,709,517. Enzalutamide is provided commercially as a soft capsule (brand name "XTANDI®") filled with a liquid comprising 40 mg of enzalutamide per one capsule and pharmaceutical excipients. The daily dosage is 160 mg, and a patient therefore needs to take four capsules daily. Among other things, a suitable single tablet of reasonable size comprising the prescribed amount of enzalutamide and having suitable and advantageous solubility and/or dissolution stability and absorption would be advantageous as a suitable alternative to soft capsules.

The patent literature reports a sparingly soluble compound held on a gel-forming water-soluble polymer such as hydroxypropyl methylcellulose or hydroxypropylcellulose, as a solid dispersion, wherein the composition contains a salt substance to improve a disintegration time and dissolution profile and the like. See, e.g., U.S. Published Patent Application No. 2002/0031547. Use of hydroxypropylmethylcellulose acetate succinate in a pharmaceutical composition comprising a sparingly soluble compound, prepared by a spray drying method, also has been reported to improve aqueous solubility and/or bioavailability. Sec. e.g., U.S. Published Patent Application No. 2002/0009494. Combining drugs with solubilizing polymers does not always improve bioavailability for a low-solubility drugs, however. Solubilization of a specific drug depends on its chemical structure and physical properties; therefore, whether any particular polymer will solubilize a specific drug is not necessarily predictable. It is often difficult and time-consuming to select polymers which achieve improved solubilization, because the drug-polymer interaction is poorly understood. For example, addition of polymers may actually speed dissolution of a drug, rather than provide enhanced concentration.

U.S. Published Patent Application No. 2017/0027910 discloses a pharmaceutical composition comprising a solid dispersion containing Enzalutamide and a polymer selected from the group consisting of hydroxypropyl methyl cellulose and hydroxypropyl methylcellulose acetate succinate, wherein the polymer is 0.5 to 7 parts by weight, with respect to 1 part by weight of the Enzalutamide U.S. Published Patent Application No. 2016/0346207 discloses solid pharmaceutical compositions comprising (a) androgen receptor antagonists; (b) a carrier and (c) a surfactant. U.S. Published Patent Application No. 2014/0378517 discloses a pharmaceutical composition comprising a solid dispersion containing Enzalutamide and a polymer selected from the group consisting of hydroxypropyl methyl cellulose and hydroxypropyl methylcellulose acetate succinate, wherein the polymer is 0.5 to 7 parts by weight, with respect to 1 part by weight of the Enzalutamide.

U.S. Published Patent Application No. 2014/0179749 discloses a pharmaceutical composition comprising solid dispersion containing Enzalutamide and a polymer. U.S. Published Patent Application No. 2014/0100256 discloses a pharmaceutical composition comprising a solid dispersion containing enzalutamide and a polymer, wherein the polymer is 0.5 to 7 parts by weight, with respect to 1 part by weight of the enzalutamide.

E.P. Published Patent Application No. 3033085 discloses dosage forms comprising Enzalutamide, wherein the Enzalutamide is present in a dissolved form. Further, E.P. Published Patent Application No. 3033085 discloses the use of a solvent having a specific HLB-value for producing a water/oil emulsion of an API having water-solubility of 1-10-3 mg/ml to 1-10-2 mg/ml. E.P. Published Patent Application No. 2895463 discloses formulations comprising amorphous Enzalutamide.

CN Published Patent Application 105030685 discloses an oral preparation of Enzalutamide solid dispersion. The oral preparation contains Enzalutamide with effective dose, and also contains a water-soluble polymer carrier for dispersing Enzalutamide, wherein the weight ratio of Enzalutamide to the water-soluble polymer carrier is 1 to 0.5-3. With the oral preparation, the solubility and the dissolution rate of Enzalutamide in the preparation is effectively improved, so that the bioavailability of Enzalutamide is improved, and the quality stability and safety of Enzalutamide are improved.

CN Published Patent Application 104857517 discloses an Enzalutamide soft capsule and a preparation method thereof. The Enzalutamide soft capsule comprises capsule content and a capsule shell, wherein the capsule content comprises Enzalutamide and pharmaceutical adjuvants; the capsule shell is formed by gelatin, glycerin, sorbitol, titanium dioxide, purified water and the like. The soft capsule can be prepared with the method comprising following steps: Labrasol, butylatedhydroxyanisole, butylatedhydroxytoluene and Enzalutamide are mixed to obtain the capsule content material of the soft capsule: the gelatin, the glycerin, the sorbitol, titanium dioxide and the purified water are mixed to obtain the capsule shell material of the soft capsule; the capsule content material and the capsule shell material of the soft capsule are pelleted on a soft capsule making machine to obtain the Enzalutamide soft capsule. The Enzalutamide soft capsule and the preparation method have the following advantages: the soft capsule is convenient to administrate and carry, the drug stability is good, effective components are dissolved quickly, and the bioavailability is high.

CN Published Patent Application 104546714 discloses an Enzalutamide micelle preparation and a preparation method thereof. The Enzalutamide micelle preparation disclosed by the invention is prepared from Enzalutamide and an amphiphilic block copolymer. The preparation method disclosed by the invention comprises the following steps of: mixing Enzalutamide with the amphiphilic block copolymer to dissolve in an organic solvent, rotatable evaporating to remove the organic solvent so as to obtain an Enzalutamide-containing film skeleton, drying, adding deionized water, ultrasonically dispersing, oscillating at constant temperature to obtain micelle solution, and adjusting the speed and centrifuging to obtain supernatant, namely the Enzalutamidenano-micelle preparation. The Enzalutamide micelle preparation prepared by the invention has the characteristics of being high in encapsulation efficiency, drug loading ratio and the like; the Enzalutamidenano-micelle is prepared by adopting an improved film dispersion method; therefore, the solubleness of Enzalutamide in water is increased; the drug loading capacity of the preparation is 6% or above; and the Enzalutamide micelle preparation is steady in structure, small in particle size and easy to store. PCT International Application WO 2016/020305 discloses process for preparing granules comprising an amorphous poorly water soluble active pharmaceutical ingredient. In this application Enzalutamide is exemplified as an amorphous poorly water soluble active pharmaceutical ingredient.

From above described prior art, it is apparent that currently available preparations of Enzalutamide are solid oral preparations e.g. tablets, capsules etc. These preparations have their own disadvantages and limitations, for example they are not suitable for all types of patient populations. Therefore there is an existing need for oral liquid pharmaceutical composition comprising Enzalutamide and more largely for Androgen Receptor Inhibitors having improved stability and palatability. Further, the oral liquid preparations are more patient compliant as compared to oral solid dosage forms. Oral solid dosage forms may not be convenient for all types of patient populations (e.g. paediatric patients) to take because of swallowing problems. Therefore it is preferable to administer active ingredient in pharmaceutical liquid dosage form.

OBJECT OF THE INVENTION

It has already been proposed that solid oral preparations as well as other route of administrations are not suitable for all types of patient populations. Therefore the principal object of the present invention is to provide oral liquid pharmaceutical preparation of Androgen Receptor Inhibitors.

Another object of present invention is to provide oral liquid composition having dose flexibility for patients who need special doses of the drug and have difficulties in swallowing oral dosage forms.

Another object of the present invention is to provide oral liquid pharmaceutical preparation of Androgen Receptor Inhibitors with sweetening agent and flavouring agent to mask the bitter taste of Androgen Receptor Inhibitors and to provide pleasant taste and therefore high patient compliance.

A further object of the present invention is to provide process for the preparation of the oral liquid pharmaceutical preparation of Androgen Receptor Inhibitors of the present invention.

A further object of the present invention is to provide use of the composition of the invention in the manufacture of a medicament. A further object of the present invention is to provide composition of the invention for use as a medicament.

A yet another object of the present invention is to provide liquid composition of Enzalutamide suitable for oral administration and process for the preparation thereof.

A yet another object of the present invention is to provide composition for use in the manufacture of a medicament for treating diseases/disorders associated with androgen receptor.

STATEMENT OF THE INVENTION

Accordingly, the present invention provides a liquid pharmaceutical composition comprising androgen receptor inhibitor and one or more pharmaceutically acceptable excipients selected from the group comprising of tillers/vehicles, solvents/co-solvents, preservatives/antioxidants, surfactants, buffering agents, chelating agents, sweetening agents, flavouring agents, sweetness/flavour enhancing agents, or combinations thereof with improved stability and palatability. Further, the liquid compositions according to the present invention shows improved dissolution profile.

There is also provided a method of preparing the liquid pharmaceutical composition comprising androgen receptor inhibitor and one or more pharmaceutically acceptable excipients selected from the group comprising of fillers/vehicles, solvents/co-solvents, preservatives/antioxidants, surfactants, buffering agents, chelating agents, sweetening agents, flavouring agents, sweetness/flavour enhancing agents, or combinations thereof.

The androgen receptor inhibitor can be selected from the group comprising Enzalutamide, Bicalutamide, Flutamide, Nilutamide, (R)-Bicalutamide, 1,1-dichloro-2,2-bis (4-chlorophenyl) ethane. MDV-3100, PF-998425, Abiraterone acetate. Cabazitaxel, Degarelix, Docetaxel, Goserelinacetate, Leuprolideacetate, Mitoxantronehydrochloride, Sipuleucel-T, Radium 223 dichloride, etc.

DETAILED DESCRIPTION OF THE INVENTION

Androgen receptor inhibitors are known to be administered through oral route of administration. Oral dosage forms include solid preparations (e.g. tablets, capsules, and powders etc.). Oral liquid preparations are more patient compliant as compared to oral solid dosage forms. Oral solid dosage forms may not be convenient for all types of patient populations (e.g. paediatric patients) to take because of swallowing problems. Therefore it is preferable to administer active ingredient in pharmaceutical liquid dosage form. Further, pharmaceutical agents (especially anticancer agents) are known to have strong bitterness which results into a bitter taste and a feeling of numbness in the mouth. Therefore oral solid dosage forms are not preferred for some types of patient population especially paediatric patient population.

Therefore in one of the embodiments, the present invention provides a pharmaceutical composition comprising androgen receptor inhibitors and one or more pharmaceutically acceptable excipients.

In one of the further embodiments, the pharmaceutical composition comprises androgen receptor inhibitors and one or more pharmaceutically acceptable excipients selected from the group comprising of fillers/vehicles, solvents/co-solvents, preservatives/antioxidants, surfactants, buffering agents, chelating agents, sweetening agents, flavouring agents, sweetness/flavour enhancing agents, or combinations thereof.

In one of the further embodiments, the pharmaceutical composition comprises androgen receptor inhibitors and one or more fillers/vehicles, one or more solvents/co-solvents, one or more preservatives/antioxidants, one or more surfactants, one or more buffering agents, one or more chelating agents, one or more sweetening agents, one or more flavouring agents, one or more sweetness/flavour enhancing agents, or combination thereof.

In one of the preferred embodiments, the pharmaceutical composition comprises androgen receptor inhibitor, a filler/vehicle, a solvent/co-solvent, a preservative/antioxidant, a surfactant, a buffering agent, a chelating agent, a sweetening agent, a flavouring agent, a sweetness/flavour enhancing agent or combination thereof.

In one of the preferred embodiments, the pharmaceutical composition is a liquid pharmaceutical composition.

In one of the preferred embodiments, the liquid pharmaceutical composition is suitable for oral administration.

In one of the further embodiments, the pharmaceutical composition is useful for the manufacture of a medicament.

In one of the further embodiments, the pharmaceutical composition is useful as a medicament.

In one of the further embodiments, the pharmaceutical composition is useful for the manufacture of a medicament for treating diseases/disorders associated with androgen receptor.

Fillers/Vehicles referred in the present invention are the liquid bases which carry drug and other excipients in dissolved or dispersed state and can be selected from either aqueous vehicles or non-aqueous vehicles. Examples of suitable aqueous vehicles are but not limited to purified water, hydro-alcoholic, polyhydric alcohols and buffers, while suitable examples of suitable non-aqueous vehicles are but not limited to vegetable oils, mineral oils, organic oily bases or emulsified bases and triglycerides. The preferred aqueous filler/vehicle is triglyceride (trade name-Kollisolv® MCT 70).

Solvents or co-solvents referred in the present invention are organic solvents used in liquid drug formulations to increase the solubility of poorly soluble substances and enhance the chemical stability of a drug. Examples of suitable solvent or co-solvents are but not limited to Water, Ethanol, Polyethylene glycols (PEG), Sorbitol, Glycerin, Propylene glycol and Benzyl alcohol. The preferred solvent is Ethanol.

Preservatives referred in the present invention are the compounds which are included in pharmaceutical dosage form to prevent the growth of microorganisms during the product's manufacture and shelf life. Examples of the suitable preservatives are but not limited to Benzyl alcohol. Chloro-butanol, Chloro-cresol, Alkyl esters of Paraben. Phenol, Phenyl ethanol, Benzoic acid, Potassium sorbate, Sodium benzoate etc. and antimicrobial solvents like Propylene glycol, Chloroform etc.

Antioxidants referred in the present invention are substances capable of inhibiting oxidation and that may be added to pharmaceutical products to prevent deterioration by oxidative processes. Examples of suitable antioxidants are but not limited to Butylatedhydroxyanisole (BHA), Butylatedhydroxy toluene (BHT), Sodium metabisulfite, Ascorbic acid, Alphatocopherol and Sodium edetate. The preferred antioxidants are BHA and BHT.

Buffering agents referred in the present invention are the compounds which provide stability and pH control to the pharmaceutical formulations. Examples of suitable buffering agents are but not limited to Sodium acetate, Sodium citrate, Ammonium sulfate. Sodium phosphate, Disodium hydrogen phosphate, Potassium citrate, Citric acid monohydrate. Trisodium citrate dihydrate.

Chelating agents referred in the present invention are the compounds which are used for drug stabilization, to maintain potency of active ingredients and to stabilize colors and flavors. Examples of suitable chelating agents are but not limited to citric acid monohydrate, disodium edetate, dipotassiumedetate, edetic acid, fumaric acid, malic acid, phosphoric acid, sodium edetate, tartaric acid and trisodiumedetate.

Sweetening agents referred in the present invention are the compounds that impart sweetness and improve patient compliance through taste masking. Examples of the suitable sweetening agents are but not limited to Sucralose, Sucrose, Acesulfame potassium. Liquid glucose, Glycerine, Sorbitol, Liquid maltitol, Saccharin sodium and Aspartame. The preferred sweetening agent is Sucralose.

Flavouring agents referred in the present invention are the compounds which are added to increase patient acceptance of the drug by masking the specific taste sensations. Examples of suitable flavouring agent are but not limited to essential oils including Peppermint oil, Orange oil, and Lemon oil etc. or can be selected from fruit flavour, e.g. Peppermint flavour, Strawberry flavour. Tutti fruity flavour, Mint flavour etc. The preferred flavouring agent is Mint flavour.

Surfactants referred in the present invention are the compounds that lower the surface tension (or interfacial tension) between two liquids or between a liquid and a solid and increase the solubility. They are also known as surface active agents. Examples of suitable surfactants are but not limited to polyoxyethylensorbitan fatty acid esters (Tween), polyoxyethylene alkyl ethers (e.g. Brij), alkylphenylpolyoxyethylene ethers (e.g. Triton-X), polyoxyethylene-polyoxypropylene copolymer (e.g. Poloxamer, Pluronic), sodium dodecyl sulphate (SDS). Labrasol. Labrasol ALF, PEG 300, PEG 400 and the like. The preferred surfactant is Labrasol/Labrasol ALF, PEG 300, PEG 400 or combination thereof.

The suitable examples of androgen receptor inhibitors are but not limited to Enzalutamide, Bicalutamide, Flutamide, Nilutamide, (R)-Bicalutamide, Topilutamide, Apalutamide (ARN-509, JNJ-56021927), Darolutamide (ODM-201, BAY-1841788), Proxalutamide (GT-0918), Saviteronel (VT-464) 1,1-dichloro-2,2-bis (4-chlorophenyl) ethane, PF-998425, Abiraterone acetate, Cabazitaxel, Degarelix, Docetaxel, Goserelin acetate. Leuprolide acetate. Mitoxantrone hydrochloride, Sipuleucel-T, Radium 223 dichloride, etc.

In one of the preferred embodiments, the androgen receptor inhibitor is Enzalutamide. In one of the further preferred embodiments, the compound Enzalutamide is in particulate form comprising particles of the compound wherein at least 90% of the particles have a particle size of less than about 20 microns.

The composition of the oral liquid formulation according to the present invention can be described in following general formula.

TABLE 1

| General formula for the liquid composition of the invention | | |
|---|---|---|
| Sr. No. | Ingredient | % w/w |
| 1 | Androgen Receptor Inhibitor | 1-30 |
| 2 | Surfactant | 30-90 |
| 3 | Antioxidant | 0-10 |
| 5 | Sweetening agent | 0-10 |
| 6 | Flavouring agent | 0-10 |
| 7 | Solvent | 0-40 |
| 8 | Filler/Vehicle | 0-40 |

In one of the further embodiments, the present invention provides process for the preparation of the pharmaceutical composition comprising androgen receptor inhibitor and one or more pharmaceutically acceptable excipients selected from the group comprising of one or more fillers/vehicles, one or more solvents/co-solvents, one or more preservatives/antioxidants, one or more surfactants, one or more buffering agents, one or more chelating agents, one or more sweetening agents, one or more flavouring agents, one or more sweetness/flavour enhancing agents, or combination thereof.

A general process for the preparation of the liquid oral pharmaceutical compositions comprising androgen receptor inhibitor and one or more pharmaceutically acceptable excipients can be described as follows. One or more pharmaceutically acceptable excipients are selected from the group comprising of fillers/vehicles, solvents/co-solvents, preservatives/antioxidants, surfactants, buffering agents, chelating agents, sweetening agents, flavouring agents, sweetness/flavour enhancing agents, or combinations thereof as described herein above.

(a) Mix one or more surfactants and one or more solvents under stirring;

(b) Dissolve androgen receptor inhibitor in the mixture obtained in Step (a);

(c) Add one or more sweetening agents in the mixture obtained in Step (b);

(d) Add one or more antioxidants in the mixture obtained in Step (c);

(e) Dilute the obtained mixture in Step (d) up to the desired volume with the filler/vehicle;

(f) Add one or more flavouring agents in the final composition obtained in Step (e).

BEST MODE OF CARRYING OUT THE INVENTION

Examples

The pharmaceutical composition of the present invention is explained in more detail with reference to the following examples. These examples are provided by way of illustration only and should not be construed as limit to the scope of the claims in any manner.

Example 1: A Liquid Oral Pharmaceutical Composition Comprising Enzalutamide

TABLE 2

| Enzalutamide liquid composition (Example-1) | | |
|---|---|---|
| Sr. No. | Ingredient | mg/5 ml |
| 1 | Enzalutamide | 160 |
| 2 | Labrasol/Labrasol ALF/PEG 300/PEG 400 or combination of solubilizer | 2600 |
| 3 | ButylatedHydroxyanisole (BHA) | 2.0 |
| 4 | Butylatedhydroxytoluene (BHT) | 0.4 |
| 5 | Sucralose | 25 |
| 6 | Mint flavour | 2.0 |
| 7 | Ethanol | 982.5 |
| 8 | Medium chain triglyceride (Kollisolv ® MCT 70) | Q.S. to 5 ml |

Method of preparation: A liquid oral pharmaceutical composition comprising Enzalutamide as active ingredient and Labrasol, ButylatedHydroxyanisole (BHA), Butylatedhydroxytoluene (BHT), Sucralose, Mint flavour, Ethanol and Kollisolv® MCT 70 was prepared following below mentioned process comprising steps of:

(a) Mix the required quantity of Labrasol/Labrasol ALF/PEG 300/PEG 400 or combination of solubilizer and Ethanol under stirring;

(b) Dissolve required quantity of Enzalutamide in the mixture obtained in Step (a);

(c) Add required quantity of Sucralose to the mixture obtained in Step (b);

(d) Add required quantity of ButylatedHydroxyanisole (BHA) and ButylatedHydroxytoluene (BHT) into the mixture obtained in Step (c);

(e) Finally dilute the mixture obtained in Step (d) to the desired volume with sufficient quantity of Kollisolv® MCT 70; and (f) Add required quantity of Mint flavour into the mixture obtained in Step (e).

Those who are skilled in the art can also understand that some variations in the herein described processes for the preparation of liquid compositions of the present invention can be adopted which are well within the skills of the skilled artisan. One can change sequences of the steps in the above mentioned process for the purposes of suitability and convenience without affecting the quality and characteristics of the resulting product. For example below mentioned alternative process can also be followed for the preparation of liquid composition of the present invention.

Example 2: A Liquid Oral Pharmaceutical Composition Comprising Enzalutamide

TABLE 3

| Enzalutamide liquid composition (Example-2) | | |
|---|---|---|
| Sr. No. | Name of Ingredients | mg/5 ml |
| 1 | Enzalutamide | 160 |
| 2 | Labrasol//Labrasol ALF/PEG 300/PEG 400 or combination of solubilizer | 3500 |
| 3 | ButylatedHydroxyanisol(BHA) | 3.5 |
| 4 | ButylatedHydroxytoluene(BHT) | 0.35 |

TABLE 3-continued

| Enzalutamide liquid composition (Example-2) | | |
|---|---|---|
| Sr. No. | Name of Ingredients | mg/5 ml |
| 5 | Sucralose | 10 |
| 6 | Mint flavour | 10 |
| 7 | Propylene Glycol | Q.S. up to 5 ml |

Method of preparation: A liquid oral pharmaceutical composition comprising Enzalutamide as active ingredient and Labrasol, ButylatedHydroxyanisole (BHA), Butylatedhydroxytoluene (BHT), Sucralose, Mint flavour, Ethanol and Propylene glycol was prepared following below mentioned process comprising steps of:

(a) Dissolve the required quantity of Labrasol/Labrasol ALF/PEG 300/PEG 400 or combination of solubilizer in Ethanol. The mixture can be heated at 50-55° C. to get clear solution;
(b) Add required quantity of ButylatedHydroxyanisole (BHA and Butylatedhydroxytoluene (BHT) in the preheated mixture obtained in Step (a) with continuous stirring to get clear solution;
(c) Cool down the solution obtained in Step (b) to 40-45° C. and add Enzalutamide into it with constant stirring for 30 minutes;
(d) Further cool down the solution obtained in Step (c) to room temperature and add required quantity of Sucralose and Mint flavour into it with constant stirring;
(e) Made up the final volume to desired quantity with propylene glycol.

Those who are reasonably skilled in the art can easily understand that similar liquid formulations using other androgen receptor inhibitors, those mentioned in the above paragraphs with other suitable excipients, also mentioned in the foregoing paragraphs may be prepared in the above mentioned formulas using above mentioned processes for preparation. Such other examples of compositions and processes of preparation thereof are also within the ambit of the invention disclosed and claimed in the present application.

Example 3: Stability Studies of the Pharmaceutical Composition Prepared in Example 1

The oral liquid pharmaceutical composition prepared according to Example 1 exhibits unexpected stability profile when tested after three (3) months under the conditions 40° C./75 RH and 25° C./60 RH. The liquid composition according to the present invention possess very less amount of impurities and highest degree of purity. The results of the stability tests conducted are summarized in the table below.

TABLE 4

Stability study results of Enzalutamide liquid composition of Example-1

| | | Results | | |
|---|---|---|---|---|
| Name of Impurity | Limit | Initial | After 3 months at 40° C./75 RH | After 3 months at 25° C./60 RH |
| Amine amide impurity | NMT 0.2% | ND | ND | ND |
| Trifluoromethyl impurity | NMT 0.2% | ND | ND | ND |
| Dioxoimidazolidine impurity | NMT 0.2% | 0.1% | 0.2% | 0.1% |
| Desfluoro impurity | NMT 0.2% | ND | ND | ND |
| Highest individual unspecified impurity | NMT 0.2% | 0.1% | 0.1% | 0.1% |
| Total amount of impurities | NMT 1.5% | 0.2% | 0.4% | 0.3% |

NMT = Not More Than;
ND = Not Detected

Example 4: Dissolution Studies of the Pharmaceutical Composition Prepared in Example 1

Apparatus: USP-II (Paddle with Sinker)

Medium: 900 ml Dissolution media

RPM: 50

Temperature: 37° C.±0.5° C.

Time point: 5, 10, 15, 20, 30, 45 and 60 minutes

Preparation of 0.1N HCl:

Dilute 85 ml of Concentrated Hydrochloric Acid to 10,000 ml with water.

Preparation of Dissolution Media (0.1N HCl+0.3% CTAB):

Add 30 g CTAB (Cctyl Tri-methyl ammonium bromide) in 10 liter 0.1N HCl. Dissolve and mix well.

Sample Preparation:

Set the dissolution parameters of the instrument as mentioned above. Place 5 ml sample in each six different vessels and operate the apparatus exactly for specific time mentioned above. At the end of specified time, withdraw about 10 mL of solution from a zone midway between the surface of the dissolution medium and top of the paddle, not less than 1 cm from the bowl wall. Filter the solution through 0.45 μm Millipore PVDF filter; collect the filtrate by discarding first 3 mL of the filtrate.

Results of the dissolution studies are summarized in the table below.

TABLE 5

Dissolution study results of Enzalutamide liquid composition of Example-1

| Time (minutes) | % Cumulative drug dissolved |
|---|---|
| 5 | 80.2 |
| 10 | 81.7 |
| 15 | 83.9 |
| 20 | 85.5 |
| 30 | 87.0 |
| 45 | 88.6 |
| 60 | 89.0 |

It should be understood that various changes and modifications to the presently preferred embodiments and examples described herein will be apparent to those skilled in the art. Such changes and modifications can be made without departing from the spirit and scope of the present subject matter and without diminishing its intended advantages. It is therefore intended that such changes and modifications be covered by the appended claims.

We claim:

1. An oral liquid formulation, comprising:

enzalutamide in an amount of 3.2% w/w;

a surfactant in an amount of from about 30% w/w to about 80% w/w;

one or more pharmaceutically acceptable excipients; and a non-aqueous vehicle.

2. The oral liquid formulation of claim 1, wherein the surfactant is selected from the group consisting of a polyoxyethylene sorbitan fatty acid ester, a polyoxyethylene alkyl ether, an alkyl phenyl polyoxyethylene ether, a polyoxyethylene-polyoxypropylene copolymer, a sodium dodecyl sulphate, a polyethylene glycol, a polyoxylglyceride, or a combination thereof.

3. The oral liquid formulation of claim 1, wherein the surfactant comprises a polyoxylglyceride.

4. The oral liquid formulation of claim 1, wherein the non-aqueous vehicle is selected from the group consisting of an oil, an emulsified base, a medium chain triglyceride, or a combination thereof.

5. The oral liquid formulation of claim 1, wherein the non-aqueous vehicle is present in an amount of from 15% w/w to about 40% w/w.

6. The oral liquid formulation of claim 1, wherein the non-aqueous vehicle comprises a medium chain triglyceride in an amount of from about 15% w/w to about 40% w/w.

7. The oral liquid formulation of claim 1, wherein the one or more pharmaceutically acceptable excipients is selected from the group consisting of a solvent/co-solvent, an antioxidant, a sweetening agent, a flavouring agent, or a combination thereof.

8. The oral liquid formulation of claim 1, wherein the one or more pharmaceutically acceptable excipients is present in an amount of from about 0.001% w/w to about 70% w/w.

9. The oral liquid formulation of claim 1, wherein the one or more pharmaceutically acceptable excipients comprises a solvent/co-solvent selected from the group consisting of an ethanol, a polyethylene glycol, a sorbitol, a glycerin, a propylene glycol, a benzyl alcohol, or a combination thereof.

10. The oral liquid formulation of claim 1, wherein the one or more pharmaceutically acceptable excipients comprises an antioxidant selected from the group consisting of a butylated hydroxy anisole, a butylated hydroxy toluene, a sodium metabisulfite, an ascorbic acid, an alpha tocopherol, a sodium edetate, or a combination thereof.

11. The oral liquid formulation of claim 1, wherein the one or more pharmaceutically acceptable excipients comprises a sweetening agent selected from the group consisting of a sucralose, a sucrose, an acesulfame potassium, a liquid glucose, a glycerin, a sorbitol, a liquid maltitol, a saccharin sodium, an aspartame, or a combination thereof.

12. The oral liquid formulation of claim 1, wherein the one or more pharmaceutically acceptable excipients comprises a flavoring agent selected from the group consisting of an essential oil, a fruit flavor, or a combination thereof.

13. A method for treating prostate cancer in a human, which comprises administering a therapeutically effective amount of the oral liquid formulation of claim 1 to the human.

14. A method for treating castration-resistant prostate cancer in a human, which comprises administering a therapeutically effective amount of the oral liquid formulation of claim 1 to the human.

15. The oral liquid formulation of claim 1, wherein the solvent/co-solvent comprises an ethanol in an amount of from about 2% w/w to about 30% w/w.

16. The oral liquid formulation of claim 1, wherein the antioxidant comprises a butylated hydroxy anisole, and a butylated hydroxy toluene in an amount of from about 0.01% w/w to about 5% w/w.

17. The oral liquid formulation of claim 1, wherein the sweetening agent comprises a sucralose in an amount of from about 0.01% w/w to about 5% w/w.

18. The oral liquid formulation of claim 1, wherein the flavouring agent comprises a fruit flavour in an amount of from about 0.01% w/w to about 5% w/w.

19. The oral liquid formulation of claim 1, wherein the flavouring agent comprises a mint flavour in an amount of from about 0.01% w/w to about 5% w/w.

20. The oral liquid formulation of claim 1, wherein the oral liquid formulation has less than 1.5% enzalutamide related substance impurities after storage at 40° C./75% RH or 25° C./60% RH for 3 months.

* * * * *